(12) United States Patent
Ouyang et al.

(10) Patent No.: US 7,407,066 B2
(45) Date of Patent: Aug. 5, 2008

(54) DOSAGE COUNTING DEVICES

(75) Inventors: Tianhong Ouyang, Chapel Hill, NC (US); Geoff Brace, Raleigh, NC (US)

(73) Assignee: Bespak, plc, King's Lynn, Norfolk (GB)

( * ) Notice: Subject to any disclaimer, the term of this patent is extended or adjusted under 35 U.S.C. 154(b) by 604 days.

(21) Appl. No.: 10/468,813

(22) PCT Filed: Feb. 22, 2002

(86) PCT No.: PCT/GB02/00767

§ 371 (c)(1),
(2), (4) Date: Mar. 9, 2004

(87) PCT Pub. No.: WO02/069252

PCT Pub. Date: Sep. 6, 2002

(65) Prior Publication Data

US 2004/0144798 A1    Jul. 29, 2004

(30) Foreign Application Priority Data

Feb. 23, 2001  (GB) ................. 0104556.6

(51) Int. Cl.
*B67D 5/22* (2006.01)
(52) U.S. Cl. .................. 222/36; 128/205.23
(58) Field of Classification Search .......... 222/36, 222/23, 30, 32, 38; 128/200.23, 205.23, 128/203.12, 203.15, 205.24; 604/58; 215/230; A61M 15/00

See application file for complete search history.

(56) References Cited

U.S. PATENT DOCUMENTS

| | | | |
|---|---|---|---|
| 5,228,586 A | 7/1993 | Fuchs | |
| 5,421,482 A | 6/1995 | Garby et al. | |
| 5,611,444 A | 3/1997 | Garby et al. | |
| 5,687,710 A | 11/1997 | Ambrosio et al. | |
| 5,718,355 A | 2/1998 | Garby et al. | |
| 5,740,972 A | 4/1998 | Matthew | |
| 5,799,651 A * | 9/1998 | Garby et al. ........... | 128/200.23 |
| 5,829,434 A | 11/1998 | Ambrosio et al. | |
| 5,988,496 A | 11/1999 | Bruna | |
| 6,161,724 A * | 12/2000 | Blacker et al. ........ | 222/23 |

(Continued)

FOREIGN PATENT DOCUMENTS

EP    0 480 488    4/1992

(Continued)

*Primary Examiner*—Lien T Ngo
(74) *Attorney, Agent, or Firm*—Smith, Gambrell & Russell, LLP

(57) ABSTRACT

Apparatus comprising a housing (1) defining a portion (2) for receiving in use a dose-dispensing container (20), the housing containing a dose counter comprising an annular counter member (40) and a driving member (41), the driving member comprising a planar ring portion (50) and first and second sets of flexible teeth (51, 52) depending from opposite sides of the planar ring portion, the first set of dependant fexible teeth (51) engaging a first series of teeth (47) formed on the annular counter member, wherein on movement of the received dose-dispensing container towards the driving member the first and second sets of dependant flexible teeth are caused to flex towards the plane of the ring portion to thereby incrementally rotate the annular counter member in a first direction relative to the housing.

8 Claims, 2 Drawing Sheets

Figure 1:
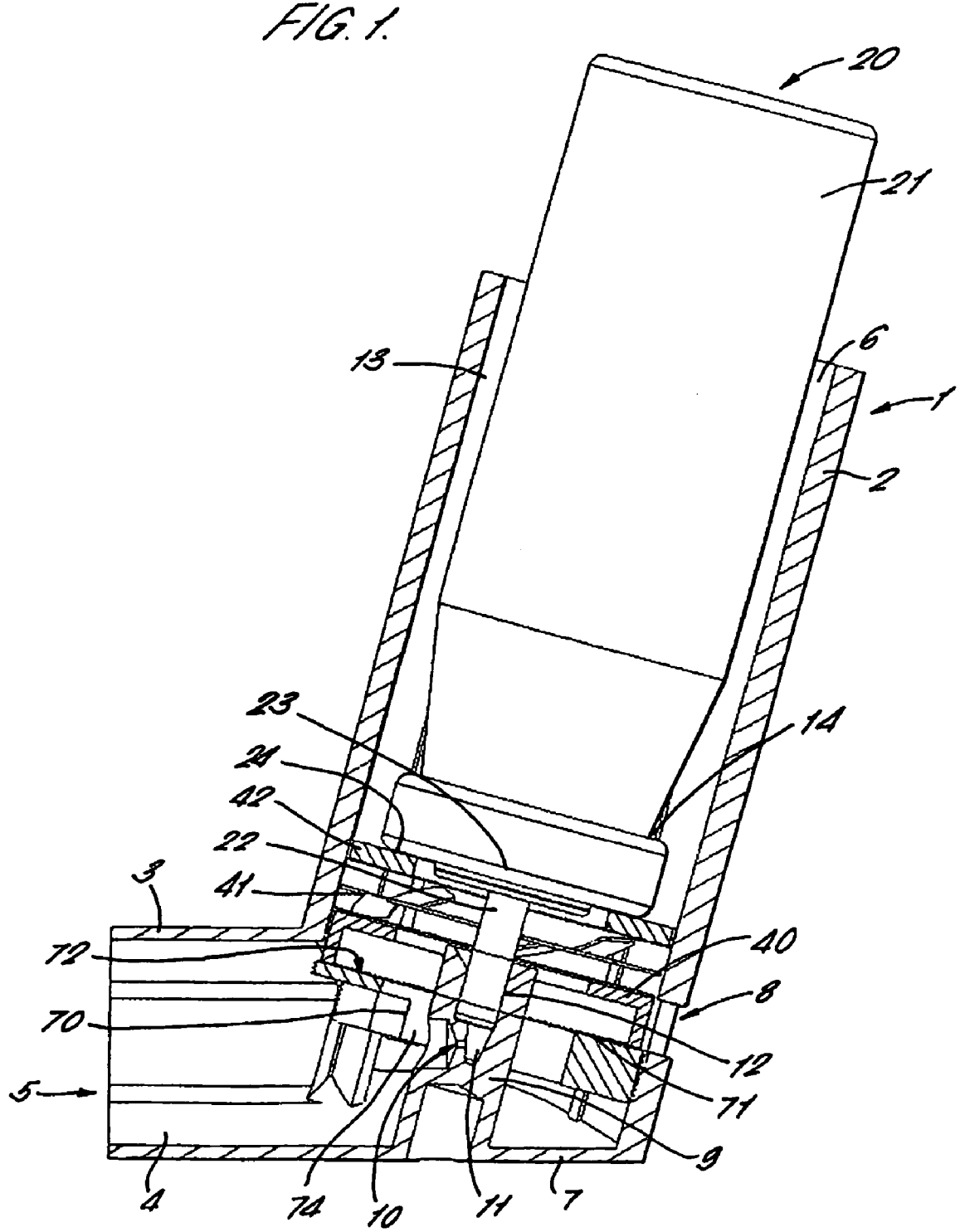

U.S. PATENT DOCUMENTS 6,164,494 A    12/2000  Marelli
6,234,168 B1 *  5/2001  Bruna .................... 128/203.12
6,679,251 B1 *  1/2004  Gallem et al. .......... 128/200.23

FOREIGN PATENT DOCUMENTS

| | | |
|---|---|---|
| EP | 1 065 477 | 1/2001 |
| GB | 1 317 315 | 5/1973 |
| GB | 2 372 541 | 8/2002 |
| GB | 2 372 542 | 8/2002 |
| GB | 2 372 543 | 8/2002 |
| WO | WO 95/08484 | 3/1995 |
| WO | WO 02/067844 | 9/2002 |
| WO | WO 02/069253 | 9/2002 |

* cited by examiner

DOSAGE COUNTING DEVICES

The present invention relates to counting devices for use with dose-dispensing delivery apparatus which require an axial force for operation.

It has been recognised that there is a need to provide accurate information to the user of a dose-dispensing delivery apparatus concerning the number of doses delivered from, or remaining in, the apparatus. Without such accurate information there is the danger that a user will forget how many doses have been delivered and hence take a greater or fewer number of doses than is required. There is also the danger that a user may be unaware that the delivery apparatus is empty or close to empty. Hence, in an emergency situation, the user may seek to take a dose from the delivery apparatus only to find that there are no doses left in the apparatus. This is especially dangerous where the delivery apparatus is for use in dispensing medicinal compounds for the treatment of chronic or acute symptoms, for example, as in the case of a pressurised metered dose inhaler used for treating asthmatic reactions.

A number of devices have been proposed to count the number of doses delivered or remaining in a delivery apparatus. WO95/08484 teaches a dose counting device for use with an aerosol medication dispenser. The device works by translating a non-rotative force on an outer cover into a rotation of an indicator wheel by use of a set of flexible pawls engaged with a set of teeth. The pawls depress and thereby extend circumferentially when the applied force forces them to effect a rotation of the teeth. This device has, however, been found to have disadvantages. The reliability of operation of the counting device depends on the relationship between the stiffness of the internal spring bias of the medication dispenser and the pawls. If the pawls are too stiff relative to the internal spring bias then the medication dispenser may dispense a dose before the pawls flex sufficiently to rotate the indicator wheel; a dose wold be delivered without the counter registering it. Alternatively, if the pawls are too flexible relative to the internal spring bias then the pawls may flex sufficiently to rotate the indicator wheel before the medication dispenser has dispensed a dose; a dose would be registered by the counter but not actually delivered.

The present invention seeks to provide a dosage counting device which overcomes these problems.

Accordingly, the present invention provides apparatus comprising a housing defining a portion for receiving in use a dose-dispensing container, the housing containing a dose counter comprising an annular counter member and a driving member, the driving member comprising a planar ring portion and first and second sets of flexible teeth depending from opposite sides of the planar ring portion, the first set of dependent flexible teeth engaging a first series of teeth formed on the annular counter member, wherein on movement of the received dose-dispensing container towards the driving member the first and second sets of dependent flexible teeth are caused to flex towards the plane of the ring portion to thereby incrementally rotate the annular counter member in a first direction relative to the housing.

The present invention also provides apparatus comprising a housing defining a portion for receiving in use a dose-dispensing container, the housing containing a dose counter comprising an annular counter member, a driving member for translating reciprocal motion of the received dose-dispensing container into rotary motion of the annular counter member, and a support member for supporting the annular counter member and driving member in proper alignment with the received dose-dispensing container, wherein the support is an interference fit in the housing such that a first actuation of the received dose-dispensing container sets the position of the support relative to the received dose-dispensing container and housing.

Figure 2:
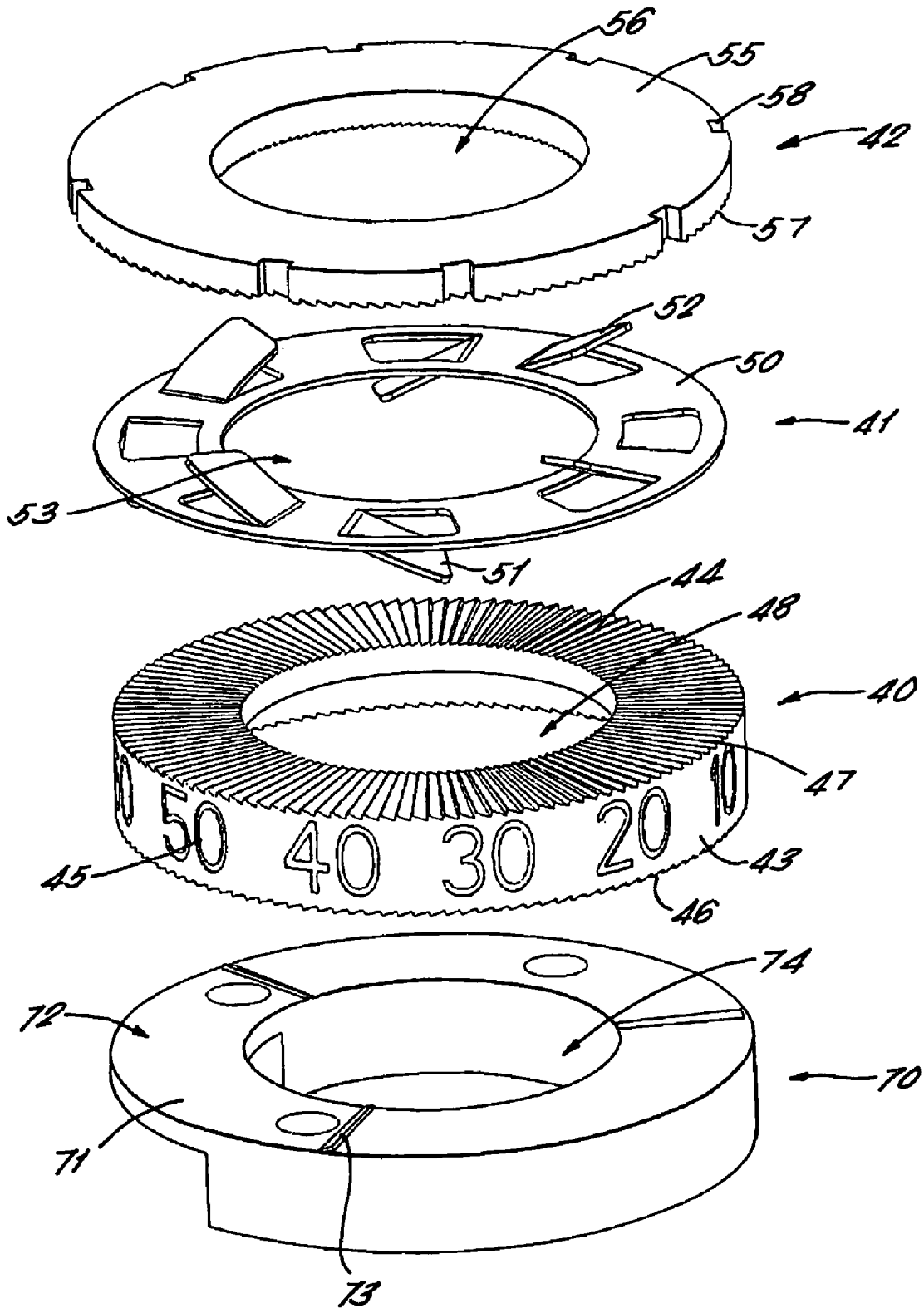

An embodiment of the present invention will now be described, by way of example only, with reference to the accompanying drawings, in which:

FIG. 1 is a cross-sectional view of a dispensing apparatus according to the present invention; and FIG. 2 is an exploded perspective view of part of the dispensing apparatus of FIG. 1.

In the following description, the invention will be illustrated, by way of example only, with respect to a pressurised dispensing container capable of delivering successive doses of a product in an aerosol form.

FIGS. 1 and 2 illustrate a dispensing apparatus comprising a housing 1 having a cylindrical portion 2 with upper and lower ends. The upper end 6 is open whilst the lower end is closed off by a basal wall portion 7. A mouthpiece 3 which communicates with the cylindrical portion 2, depends laterally from the lower end of the cylindrical portion 2. The mouthpiece 3 defines an outlet duct 4 which terminates in an outlet 5 of the mouthpiece 3.

An inwardly directed valve stem receiving block 9 is integrally formed with the basal wall portion 7 and has its longitudinal axis aligned co-axially with a longitudinal axis of the cylindrical portion 2 of the housing 1. The valve stem receiving block 9 defines a receiving bore 12 which is open to the cylindrical portion 2 and an orifice 10 which is open to the outlet duct 4 of the mouthpiece 3. The receiving bore 12 and orifice 10 are linked by a duct 11.

Eight circumferentially spaced inwardly directed longitudinal ribs 14 are provided on the internal wall of the cylindrical portion 2.

In use a pressurised dispensing container 20 is received in the cylindrical portion 2. The pressurised dispensing container 2 comprises a canister body 21 defining a storage chamber for housing the product to be dispensed. The canister body 21 is closed off at one end by a metering valve (not shown) having a valve stem 22 which extends externally from the metering valve. The metering valve is retained in the canister body by a crimped ferrule 23.

When the pressurised dispensing container 20 is inserted into the housing 1, the valve stem 22 is received in receiving bore 12 of the valve stem receiving block 9. An annular air gap 13 exists between the internal wall of the cylindrical portion 2 and the canister body 21 to allow air to flow through the dispensing apparatus in use.

According to the present invention, a dosage counter is provided in housing 1. The counter comprises an indicator wheel 40, toothed wheel 41, bearing plate 42 and support ring 70. Each of the indicator wheel 40, toothed wheel 41, bearing plate 42 and support ring 70 are generally annular in form. The indicator wheel 40 comprises a peripheral wall 43 on which are marked indicia 45 in the form of numerals. An annular flange portion 44 depends from an upper edge of the peripheral wall 43 and defines a central aperture 48. The upper surface of annular flange portion 44 is formed into a series of teeth which will be denoted as the upper teeth 47 of the indicator wheel 40. The lower edge of the peripheral wall 43 is formed into a series of teeth which will be denoted as the lower teeth 46 of the indicator wheel 40.

The toothed wheel 41 comprises a generally planar annular disc 50 formed from an elastic material such as sheet metal. A series of circumferentially spaced teeth are formed in the annular disc 50. Alternate teeth are directed upwardly and downwardly to depend out of the plane of the disc 50 to form upwardly directed teeth 52 and downwardly directed teeth 51. A central aperture 53 is defined at a centre of the annular disc 50.

The bearing plate 42 also comprises an annular disc 55 defining a central aperture 56. A lower face of the annular disc 55 is formed into a series of teeth which will be denoted as the lower teeth 57 of the bearing plate 42. A series of eight circumferentially spaced notches 58 are formed in the periphery of the bearing plate 42.

The support ring 70 comprises an annular disc 71 whose upper face 72 is formed into a series of teeth which will be denoted as the upper teeth 73 of the support ring. The annular disc 71 defines a central aperture 74.

The indicator wheel 40, toothed wheel 41, bearing plate 42 and support ring 70 are assembled in the housing 1 as follows:

The support ring 70 is positioned lowermost. Above the support ring 70 is positioned the indicator wheel 40. Above the indicator wheel 40 is positioned the toothed wheel 41. Above the toothed wheel 41 is positioned the bearing plate 42.

The support ring 70 forms a push-fit with the internal wall of the cylindrical portion 2 of the housing 1. The support ring 70 is pushed down the cylindrical portion 2 so that its central aperture 74 is received over the valve stem receiving block 9. The indicator wheel 40 is supported by the support ring 70 with the lower teeth 46 of the indicator wheel 40 engaging the upper teeth 73 of the support ring 70. As shown, the teeth 46, 73 of the indicator wheel 40 and support ring 70 are sloped relative to one another so as only to allow the indicator ring 40 to rotate relative to the support ring 70 in an anti-clockwise direction as discussed below.

The toothed wheel 41 is supported by the indicator wheel 40 with the downwardly directed teeth 51 of the toothed wheel 41 engaging the upper teeth 47 of the indicator wheel 40. As shown, the teeth 51, 47 of the toothed wheel 41 and indicator wheel 40 are sloped relative to one another so as only to allow the indicator wheel 41 to rotate relative to the toothed wheel 41 in an anti-clockwise direction as discussed below.

The bearing plate 42 is supported by the toothed wheel 41 with the lower teeth 57 of the bearing plate 42 engaging the upwardly directed teeth 52 of the toothed wheel 41. As shown, the teeth 57, 52 of the bearing plate 42 and toothed wheel 41 are sloped relative to one another so as only to allow the toothed wheel 41 to rotate relative to the bearing plate 42 in an anti-clockwise direction, as discussed below. The notches 58 engage the longitudinal ribs 14 of the housing 1 to prevent the bearing plate 42 rotating relative to the housing 1 whilst allowing relative axial movement therebetween.

During assembly, the indicator wheel 40, toothed wheel 41, bearing plate 42 and support ring 70 are inserted before the pressurised dispensing container 20. The valve stem 22 passes through the central apertures 56 and 53 of the bearing plate 42 and toothed wheel 40 before being received in the bore 12 of the valve stem receiving block 9. A leading face 24 of the ferrule 23 bears against the bearing plate 42.

In use, a user operates the pressurised dispensing container 21 by depressing the canister body 21 axially to move it relative to the cylindrical portion 2 of the housing 1. As a result, the valve stem 22 is inwardly retracted relative to the metering valve such that a dose of product is dispensed from the valve stem 22 into the bore 12 and duct 11 of the valve stem receiving block 9. The product is then channelled by duct 11 and dispensed as an aerosol through orifice 10 into the outlet duct 4. The aerosol is inhaled by a user inhaling on outlet 5 of the mouthpiece 3.

According to the present invention, as the canister body 21 is axially depressed, the leading face 24 of the ferrule 23 bears against and axially displaces the bearing plate 42.

During this axial movement the bearing plate 42 is prevented from rotating because of the engagement of the longitudinal ribs 14 in the notches 58.

The force needed to slide the support ring 70 relative to the cylindrical portion 2 is significantly greater than that needed to actuate the metering valve. Hence, during a normal operating cycle support ring 70 does not move axially. Consequently, indicator wheel 40 is prevented from moving axially. As a result, axial movement of the bearing plate 42 acts to compress the toothed wheel 41 such that the downwardly and upwardly directed teeth 51, 52 are brought towards, and into, the plane of the annular disc portion 50. This movement causes the indicator wheel 40 to rotate by an increment.

When the user releases the canister body 21, the canister body 21 returns to its original position due to the internal spring bias of the metering valve. At the time, the bias of the downwardly and upwardly directed teeth 51, 52 of the toothed wheel 50 act to push apart the indicator wheel 40 and bearing plate 42, back into their rest positions. The angling of the teeth on the bearing plate 42, toothed wheel 41, indicator wheel 40 and support ring 70 prevent any reverse movement of the indicator wheel 40 during this part of the operating cycle.

Therefore, on each actuation of the pressurised dispensing container 20 the indicator wheel 40 is rotated an increment such that the subsequent indicia 45 is visible through the viewing window 8 in the housing 1.

The dosage counter is 'set' in the housing 1 on the first actuation as follows:

The support ring 70 is assembled in the cylindrical portion 2 of the housing 1 at a point above its normal operating position, i.e., nearer the open end 6 of the housing 1 than shown in FIG. 1.

Consequently, the indicator wheel 40, toothed wheel 41 and bearing plate 42 are all also nearer the open end 6 that their normal operating positions. On the first actuation, which may be undertaken by the user or at the point of manufacture or sale, the leading face 24 of the ferrule 23 initially axially moves the bearing plate 42 without moving the support ring 70. Once the toothed wheel 41 has been completely compressed (during which movement the metering valve is actuated), the user, pharmacist or manufacturer applies a higher axial force to the canister body 21 to move both the bearing plate 42 and support ring 70 axially until the retracted valve stem 22 'grounds' against the base of the receiving bore 12 of the valve stem receiving block 9. The support ring 70 is now in its normal operating position and is 'set'. The setting of the support ring 70 takes into account any variations in distance between the leading face 24 of the ferrule 23 and the end of the valve stem 22. Without this feature, it is possible for variations in pressurised dispensing containers to mean that in certain circumstances, the metering valve may be actuated before the indicator wheel 40 rotates or vice versa.

The invention claimed is:

1. Apparatus comprising a housing defining a portion for receiving in use a dose-dispensing container, the housing containing a dose counter comprising an annular counter member and a driving member, the driving member comprising a planar ring portion and first and second sets of flexible teeth depending from opposite sides of the planar ring portion, the first set of dependent flexible teeth engaging a first series of teeth formed on the annular counter member, wherein on movement of the received dose-dispensing container towards the driving member the first and second sets of dependent flexible teeth are caused to flex towards the plane of the ring portion to thereby incrementally rotate the annular counter member in a first direction relative to the housing.

2. Apparatus as claimed in claim 1 further comprising a support member slidably received in the housing to support the annular counting member and driving member in proper alignment.

3. Apparatus as claimed in claim 2 wherein the support member comprises a series of teeth engagable with a second series of teeth formed on the annular counter member, so as to prevent rotation of the annular counter member in a direction opposed to the first direction.

4. Apparatus as claimed in claim 1 wherein the dose counter further comprises a bearing member against which a surface of the received dose-dispensing container bears, the bearing member comprising a series of teeth engagable with the second set of dependent flexible teeth of the driving member, such that movement of the bearing member towards the driving member causes the driving member to rotate relative to the bearing member.

5. Apparatus as claimed in claim 1 wherein the annular counter member comprises a series of indicia around its periphery.

6. Apparatus as claimed in claim 5 wherein the indicia are visible to a user through a window formed in the housing.

7. Apparatus as claimed in claim 1 wherein the driving member is formed from sheet metal.

8. Apparatus as claimed in claim 7 wherein the teeth of the driving member are dependent flanges pressed from the sheet metal.

* * * * *